(12) United States Patent
Erickson et al.

(10) Patent No.: US 7,331,263 B2
(45) Date of Patent: Feb. 19, 2008

(54) SURGICAL SCREWDRIVERS WITH TORQUE CONTROL AND METHODS OF USE

(75) Inventors: David R. Erickson, Memphis, TN (US); Wilder Companioni, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 10 days.

(21) Appl. No.: 11/394,453

(22) Filed: Mar. 31, 2006

(65) Prior Publication Data

US 2007/0227314 A1 Oct. 4, 2007

(51) Int. Cl.
*B25B 23/155* (2006.01)
*A61B 17/58* (2006.01)

(52) U.S. Cl. .................................. 81/467; 606/104
(58) Field of Classification Search ............... 81/467, 81/471; 606/104
See application file for complete search history.

(56) References Cited

U.S. PATENT DOCUMENTS

| | | | | |
|---|---|---|---|---|
| 3,485,117 A | * | 12/1969 | Tyrrell et al. ............... | 81/477 |
| 4,611,515 A | * | 9/1986 | Marbourg, Jr. ............. | 81/454 |
| 5,176,050 A | * | 1/1993 | Sauer et al. ................ | 81/471 |
| 5,295,831 A | * | 3/1994 | Patterson et al. ........... | 433/141 |
| 5,347,894 A | | 9/1994 | Fischer | |
| 5,433,665 A | | 7/1995 | Beaty et al. | |
| 5,464,407 A | | 11/1995 | McGuire | |
| 5,681,135 A | | 10/1997 | Simonson | |
| 5,704,261 A | * | 1/1998 | Strauch et al. ............. | 81/467 |
| 5,797,918 A | | 8/1998 | McGuire et al. | |
| 5,868,047 A | * | 2/1999 | Faust et al. ................ | 81/438 |
| 6,132,437 A | | 10/2000 | Omurtag et al. | |
| 6,155,147 A | | 12/2000 | Dzieman | |
| 6,269,716 B1 | | 8/2001 | Amis | |
| 6,308,598 B1 | * | 10/2001 | O'Neil ...................... | 81/467 |
| 6,478,795 B1 | | 11/2002 | Goumay et al. | |
| 6,752,808 B2 | * | 6/2004 | Schumacher ............... | 606/90 |
| 6,799,480 B1 | | 10/2004 | Walsh et al. | |
| 7,107,883 B2 | * | 9/2006 | Casutt ....................... | 81/467 |

OTHER PUBLICATIONS

Enius® Tools. "Wheel Torque Tools." 2 pages. pp. 255 and 256.
Westlake Plastics Company. "Pomalux®." 2005. 1 page. http://www.westlakeplastics.com/viewresults.asp?productname=Polmalux®&busgrp=CM.

* cited by examiner

*Primary Examiner*—David B Thomas
(74) *Attorney, Agent, or Firm*—Coats & Bennett, P.L.L.C.

(57) ABSTRACT

The present application is directed to screwdrivers and methods of use for applying a controlled amount of torque to a fastener. In one embodiment, the screwdriver includes a shaft constructed of a material that is deformable upon the application of an excessive amount of torque. The deformation may cause the screwdriver to disengage from the fastener. In one embodiment, the tip of the shaft that engages the fastener is constructed of a material that deforms when an excessive amount of torque is applied to the fastener. The deformation causes the tip to disengage from the fastener. The deformation prevents the screwdriver from applying an amount of torque above a predetermined limit.

26 Claims, 7 Drawing Sheets

SURGICAL SCREWDRIVERS WITH TORQUE CONTROL AND METHODS OF USE

BACKGROUND

The present application is directed to surgical screwdrivers for inserting a fastener into a patient and, more particularly, to screwdrivers and methods of use that control the amount of torque that can be applied to a fastener.

Various surgical procedures utilize one or more fasteners that are attached within the patient. The fasteners include a shaft that is inserted into a support member such as an implant, bone, or tissue. The fastener further includes a head positioned at an end of the shaft that includes a receiver for engagement with a screwdriver. The shaft may include threads to assist in inserting the screw into the support member and in preventing the screw from backing out of the support member. The head may include a variety of different receivers with different shapes and sizes depending upon the context of use.

The screwdriver includes a tip that engages the receiver and a shaft to rotate the fastener and drive it into the support member. The screwdriver may further include a handle that is grasped and rotated by the surgeon to insert the fastener into the support member.

One potential problem with previous screwdrivers is the amount of torque that is applied to the fastener. In some instances, the fastener could shear if excessive torque is applied through the screwdriver. The shear often occurs in the fastener between the connection of the head and the shaft. Further, fasteners may be constructed of a polymeric material that is relatively weak compared to the strength of metal. These fasteners are particularly prone to shear when exposed to an excessive amount of torque.

SUMMARY

The present application is directed to screwdrivers and methods of use for inserting a fastener into a support member. The screwdriver is constructed to prevent application of torque above a predetermined amount. In one embodiment, the screwdriver includes a shaft that is elastically deformable when exposed to an excessive torque. The geometry may cause a tip of the screwdriver to disengage from the fastener when the shaft elastically deforms. In one embodiment, the tip is constructed of a deformable material. The tip deforms when exposed to excessive torque and may disengage from the fastener.

DETAILED DESCRIPTION

The present application is directed to screwdrivers and methods of use for applying a controlled amount of torque to a fastener. In one embodiment, the screwdriver includes a shaft constructed of a material that is deformable upon the application of an excessive amount of torque. The shaft deformation may be elastic, plastic, or some combination thereof. The shaft deformation may cause the screwdriver to disengage from the fastener. In one embodiment, the tip of the shaft that engages the fastener is constructed of a material that is also deformable when an excessive amount of torque is applied to the fastener. The tip deformation may be elastic, plastic, or some combination thereof. The deformation causes the tip to disengage from the fastener. One or both of the shaft deformation and the tip deformation prevents the screwdriver from applying an amount of torque above a predetermined limit.

Figure 1:
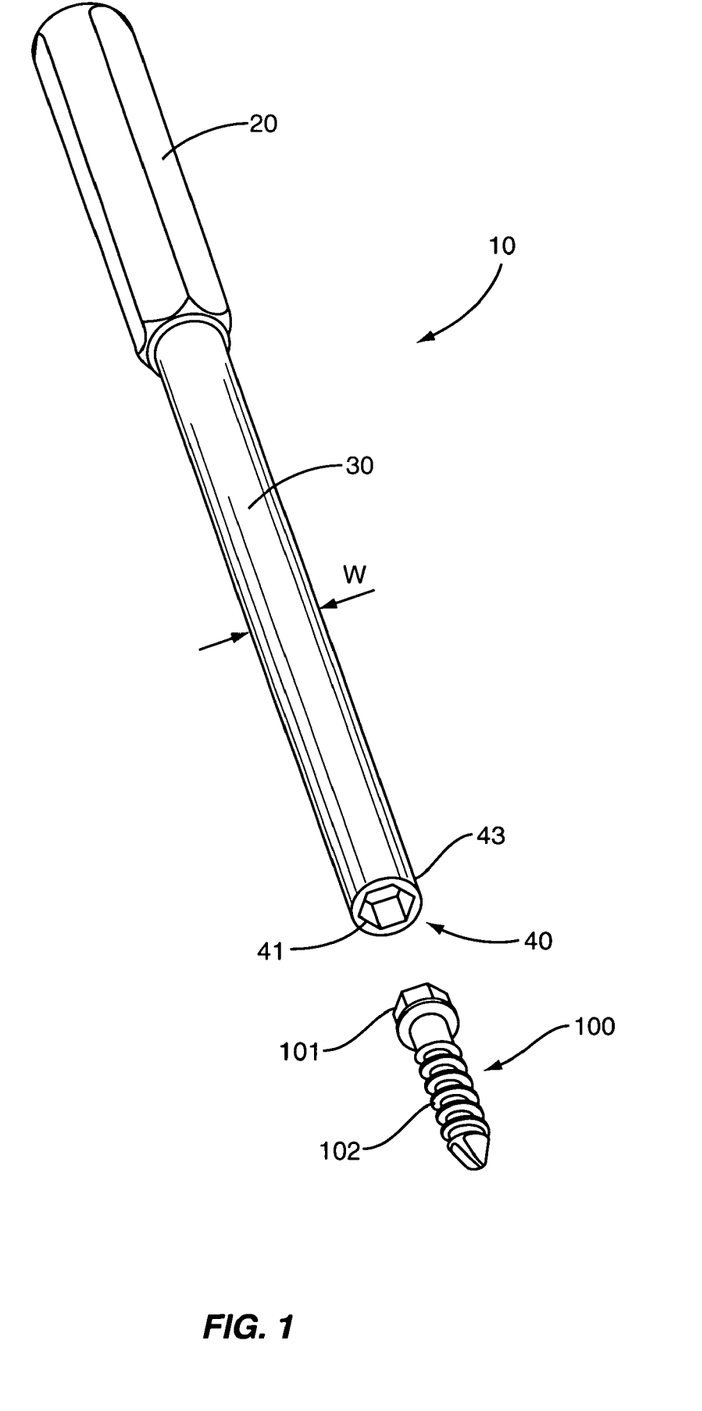
FIG. 1 is a perspective view illustrating a screwdriver according to one embodiment.

FIG. 1 illustrates one embodiment of a screwdriver 10. The screwdriver 10 includes a shaft 30 with a tip 40 at a distal end and a handle 20 at a proximal end. The tip 40 engages the shaft 30 and the handle 20 with the fastener 100. In one embodiment as illustrated in FIG. 1, tip 40 includes an aperture 41 with a depth that extends into the shaft 30 from a distal edge 43. The aperture 41 may extend into the shaft 30 a variety of distances. In one embodiment, the depth of the aperture 41 is relatively shallow to receive the head 101 of the fastener 100. In one embodiment, the depth is larger and head 101 and all or a portion of the shaft 102 may extend into the aperture 41.

Figure 2:
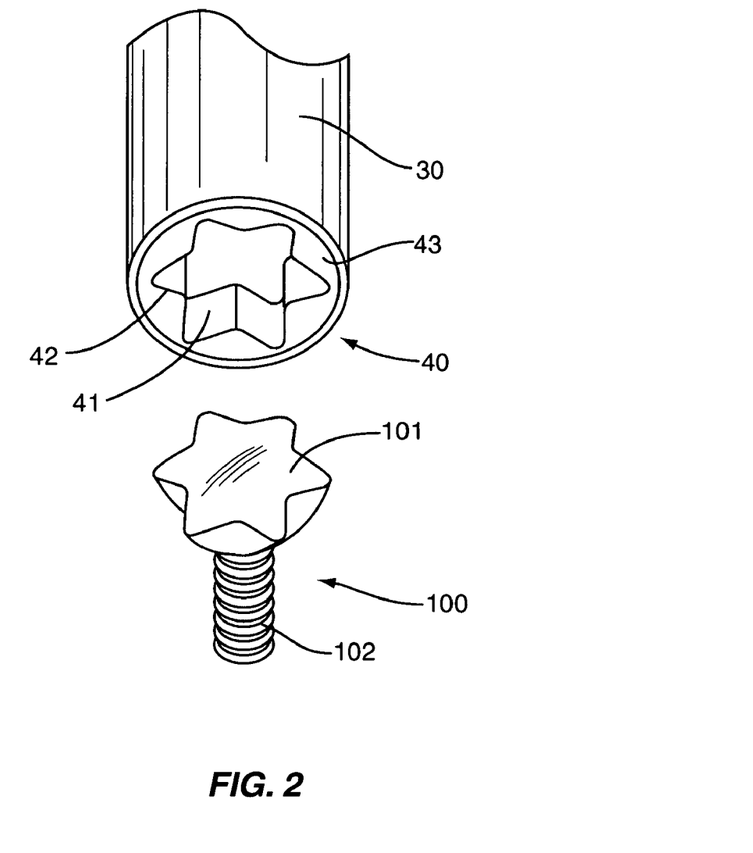
FIG. 2 is a partial perspective view illustrating a tip of a screwdriver and a fastener according to one embodiment.
Figure 3:
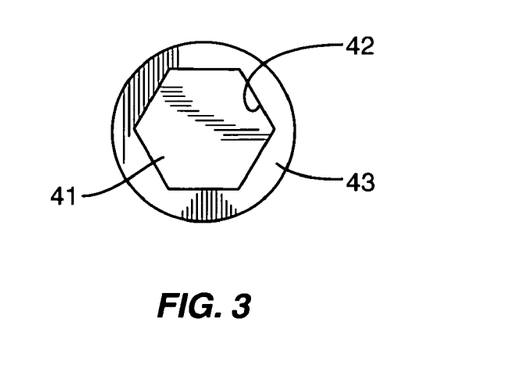
FIG. 3 is a bottom view illustrating a tip according to one embodiment.

The aperture 41 may have a variety of shapes and sizes to engage with the fastener 100. FIG. 2 illustrates one embodiment with the aperture 41 comprising edges 42 that form a variety of arms that extend outward from a central section. In one embodiment, the aperture 41 is shaped to receive a hexalobular or star-shaped drive screw. FIG. 3 illustrates one embodiment with the aperture 41 including a polygonal shape defined by edges 42. The aperture 41 may further be chamfered to assist with disengagement of the fastener 100.

In one embodiment, the aperture 41 is centered within the shaft 30 with the distal edge 43 extending around the periphery of the aperture 41. In one embodiment, the distal edge 43 is substantially straight across the tip 40 as illustrated by the line Y in FIG. 4. This configuration causes the edges of the shaft 30 that form the aperture 41 to extend a substantially equal amount around the fastener 100. This configuration contains the fastener 100 securely within the aperture 41. In one embodiment, line Y formed by the distal edge 43 is substantially perpendicular to a reference line X that extends through the shaft 30.

The fastener 100 may have a variety of shapes and sizes. In one embodiment as illustrated in FIG. 2, fastener 100 includes a head 101 and a shaft 102. In one embodiment, fastener 100 is a screw with the head 101 being shaped and sized to engage with the tip 41 and the shaft 102 including helical threads. In one embodiment, fastener 100 is constructed of a resorbable material comprising polymers and/or co-polymers made from lactic acid and/or glycolic acid. In one embodiment, the fastener 100 is constructed of metal.

Figure 4:
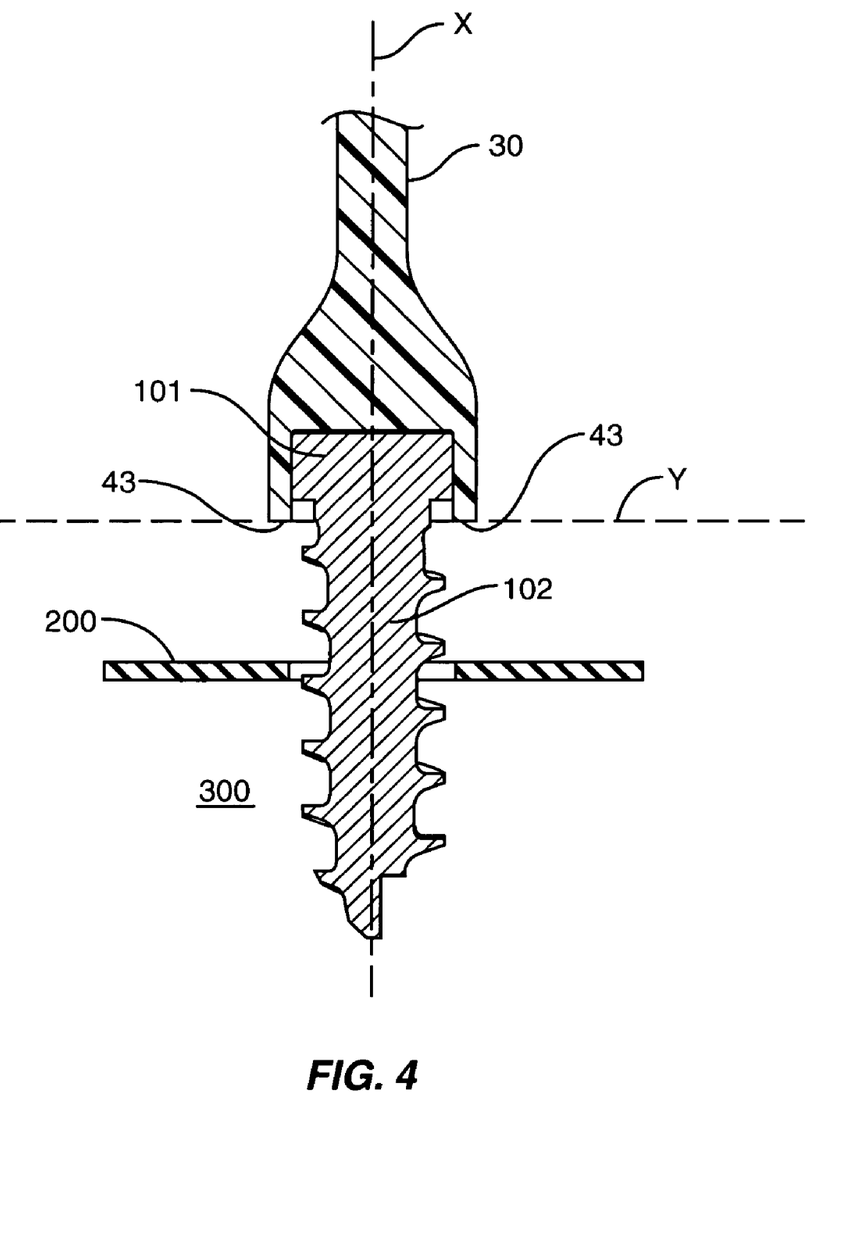
FIG. 4 is a cross section view illustrating a tip engaged with a fastener according to one embodiment.

The fastener 100 has a shape that may tend to shear at the connection between the head 101 and the shaft 102. In one embodiment as illustrated in FIG. 4, the fastener 100 attaches a plate 200 to the support member 300.

Figure 5:
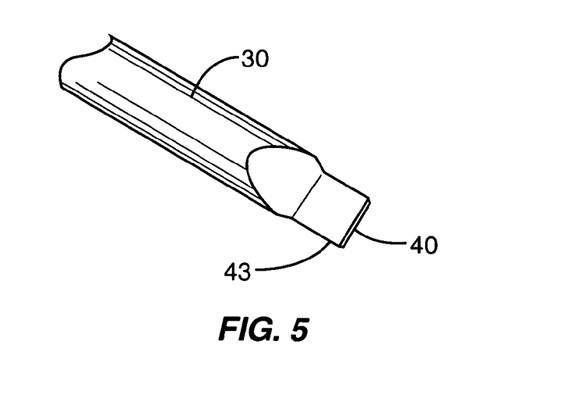
FIG. 5 is a partial perspective view illustrating a tip according to one embodiment.
Figure 6:
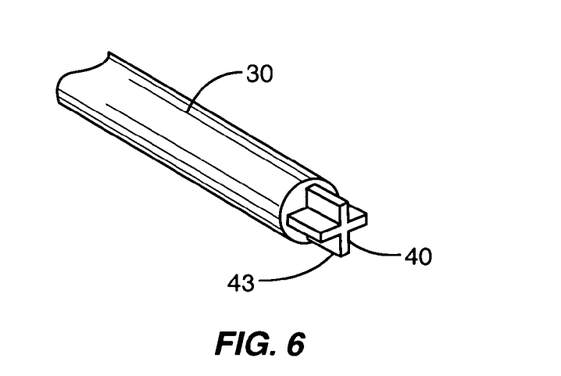
FIG. 6 is a partial perspective view illustrating a tip according to one embodiment.

In one embodiment, the tip 40 of the screwdriver 10 extends outward from the shaft 30 with the distal edge 43 configured to engage the fastener 100. FIG. 5 illustrates one embodiment shaped to engage with a flathead fastener. FIG. 6 illustrates an embodiment shaped to engage a Philips fastener. Additional shapes may be available to engage the fastener and include but not limited to Allen, SupaDriv, TORX, PoziDriv, and Robertson.

Figure 7:
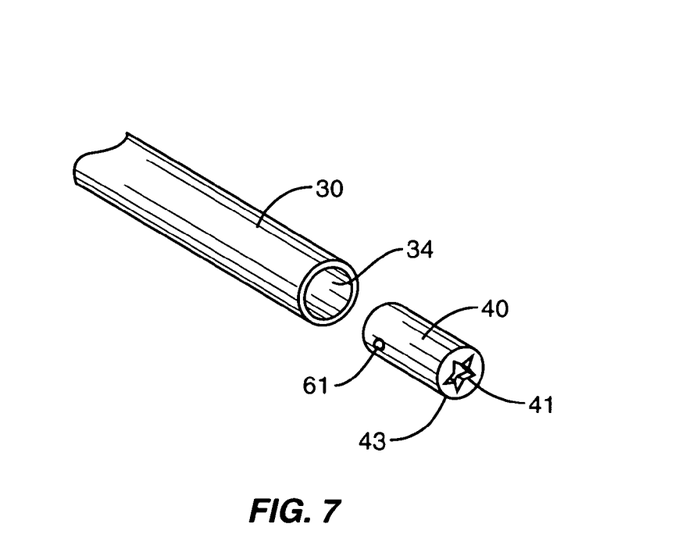
FIG. 7 is a partial perspective view illustrating a tip according to one embodiment.

In one embodiment, the tip 40 is integral with the shaft 30 such as illustrated in FIG. 1. In another embodiment as illustrated in FIG. 7, the tip 40 is a separate member that attaches to the shaft 30. In the embodiment of FIG. 7, shaft 30 includes an opening 34 sized to receive the tip 40. The tip 40 fits within the opening 34 and the distal edge 43 may extend outward a variety of lengths. In one embodiment, the tip 40 locks within the opening 34 to prevent inadvertent removal. In one embodiment, a ball (not illustrated) within the opening 34 engages a detent 61 on the tip 40. The tip 40 may include an arm that engages a connection with in the opening 34 when the tip 40 is inserted and rotated within the opening 34. The tip 40 may also be maintained by a friction fit, or by magnetic forces.

In one embodiment, tip 40 is constructed of a material that plastically deforms when exposed to an excessive amount of torque. Examples of the material may include polyethylene, ultra-high-molecular-weight-poly-ethylene (UHMWPE), polytetrafluoroethylene, polyurethane, polyester, acetal copolymer, Pomalux, Ultem, Nylon, and Pebax.

The tip 40 may include a first shape when less than a predetermined amount of torque is applied. FIGS. 5 and 6 illustrate embodiments of a tip 40 in a first shape. This shape engages with the fastener 100 and the material includes a stiffness to transfer the torque applied through the shaft 30 to the fastener 100. When exposed to an amount of torque above a predetermined limit, the tip 40 plastically deforms and the shape changes away from the first shape. The shape change disengages the fastener 100 and prevents the torque applied to the shaft 30 from transferring to the fastener 100. In one embodiment, the shape deforms based on the amount of applied torque with greater torque resulting in greater deformation. In one embodiment, the deformation is elastic and the tip returns to the first shape after removal of the torque. In one embodiment, the deformation is plastic and the tip remains substantially in a deformed shape even after the applied torque is removed. Plastically deformed tips 40 may be discarded after use.

Handle 20 provides a surface for grasping and manipulating the screwdriver 10. Handle 20 is grasped by the surgeon and rotated to apply torque to the fastener 100. Handle 20 may also be used to apply a downward force to further facilitate insertion of the fastener 100. In one embodiment, handle 20 is positioned on a proximal end of the shaft 30. In another embodiment, handle 20 is positioned along a central section of the shaft 30. In one embodiment, two or more handles 20 are positioned along the shaft 30. In one embodiment, handle 20 includes a width that is greater than the shaft 30. Handle 20 may include a varying width having relatively wide and narrow sections. Handle 20 may further include an ergonomic shape. In one embodiment, handle 20 includes a knurled or textured surface to prevent slippage. In one embodiment, the handle 20 is removably attached to the shaft 30. In one embodiment, the shaft 30 is connected to a powered rotational device and there is no handle 20.

Shaft 30 may have a variety of lengths depending upon the context of use. In one embodiment, shaft 30 has a length for the tip 40 to be positioned within the patient with the handle 20 exterior to the patient. Shaft 30 may further have a variety of cross-sectional shapes including circular, rectangular, polygonal, etc. In one embodiment, the shaft 30 may have an asymmetric cross section that tends to buckle when the shaft 30 is subjected to a predetermined amount of torque. In one embodiment, the shaft 30 is solid. In another embodiment, the shaft 30 is hollow. In another embodiment, one or more sections of the shaft 30 are solid with the remainder being hollow.

Figure 8:
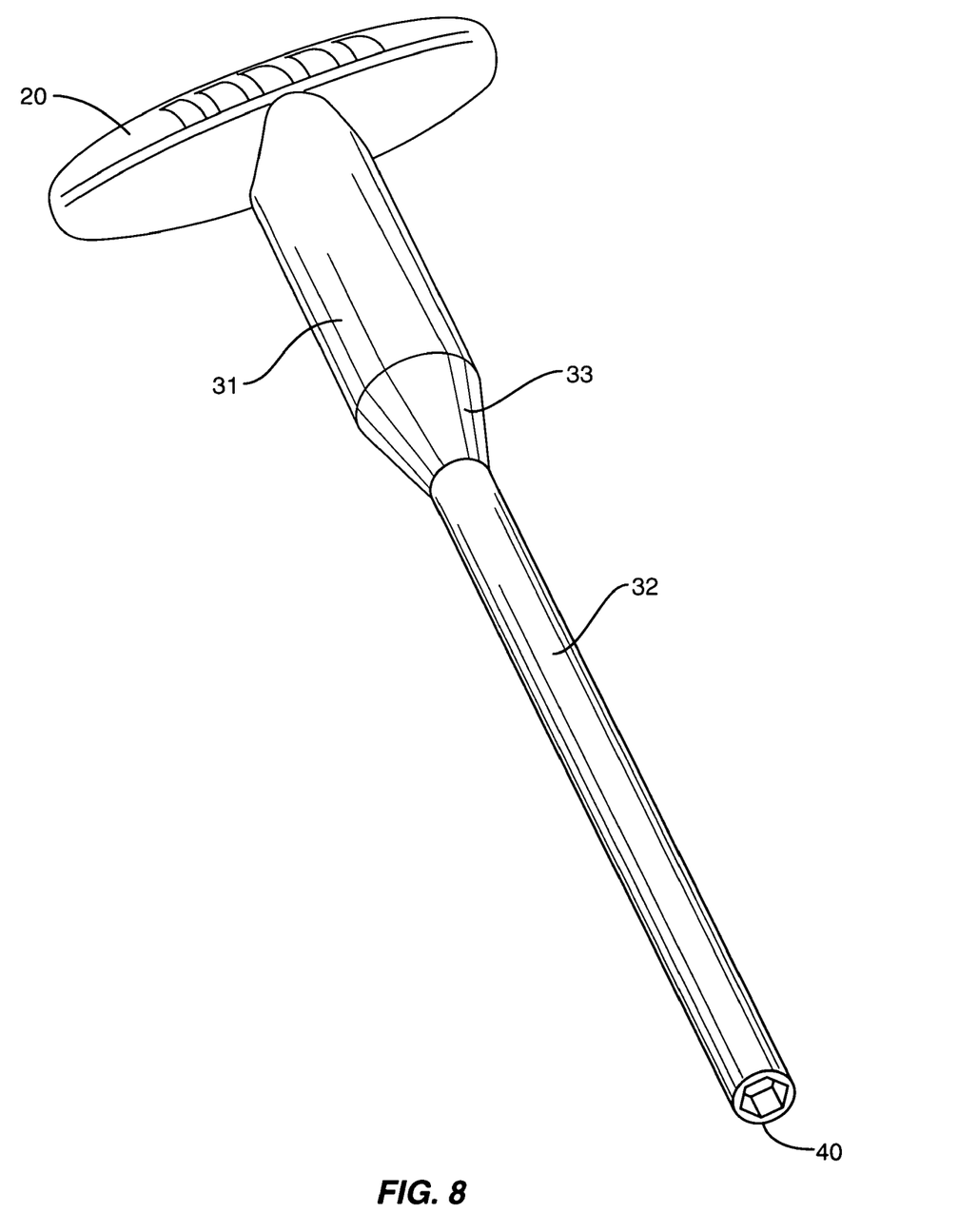
FIG. 8 is a perspective view illustrating a screwdriver according to one embodiment.
Figure 9:
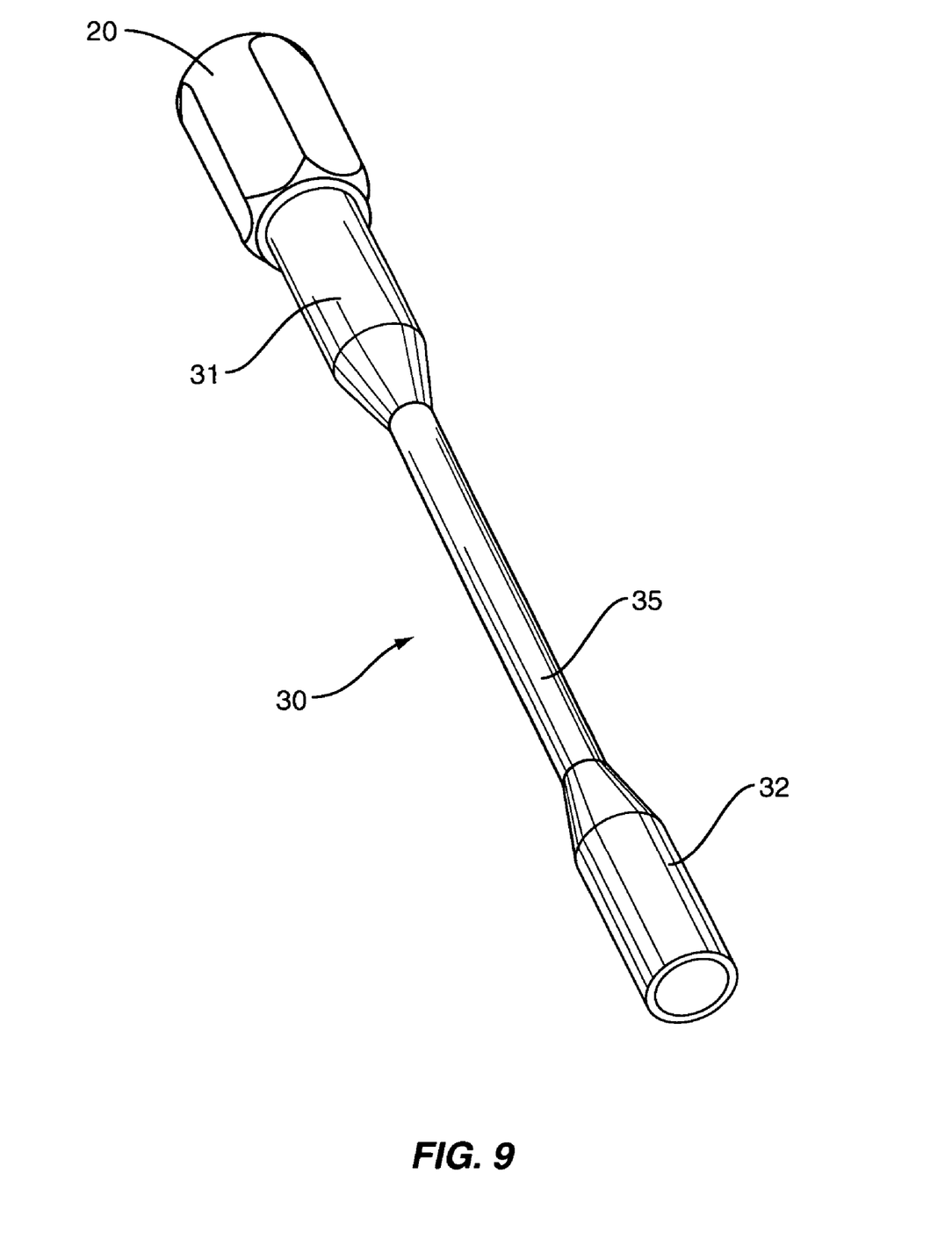
FIG. 9 is a perspective view illustrating a screwdriver according to one embodiment.

In one embodiment as illustrated in FIG. 1, the width w is substantially constant. In another embodiment, the width w tapers downward from a larger width at the handle 20 and a smaller width at the tip 40. FIG. 8 illustrates an embodiment with the shaft 30 including a first section 31 with a first width and a second section 32 with a second width. In this embodiment, a tapered section 33 transitions the first and second sections 31, 32. FIG. 9 illustrates one embodiment with first and second sections 31, 32 separated by a neck 35. In this embodiment, neck 35 includes a smaller width than the sections 31, 32. Sections 31, 32 may include the same or different widths.

The shaft 30 may be constructed from a variety of materials. Examples of the shaft material may include polyethylene, ultra-high-molecular-weight-poly-ethylene (UHMWPE), polytetrafluoroethylene, polyurethane, polyester, acetal copolymer, Pomalux, Ultem, Nylon, and Pebax. In one embodiment, the entire shaft 30 is constructed form the same material. In another embodiment, one or more sections are constructed from a first material, and other sections are constructed from other materials. In one embodiment, the shaft 30 and the tip 40 are constructed from the same materials. In another embodiment, the shaft 30 and tip 40 are constructed from different materials.

In one embodiment, the shaft 30 is constructed of a material that elastically deforms under a predetermined torque. The predetermined torque is set at a level to be below a torque that would cause the fastener 100 to shear. In one embodiment, the shaft 30 is substantially straight when exposed to a torque of less than the predetermine amount. The shaft includes a rotational stiffness to engage and rotate the fastener 100 during insertion into the support 300. In one embodiment, as the fastener 100 nears full insertion into the support 300, the amount of torque needed to continue rotation increases. In one embodiment, the shaft 30 gradually begins to bend as the amount of necessary torque approaches the predetermined amount. In one embodiment, the shaft 30 suddenly bends at the predetermined amount of torque. This bending prevents the screwdriver 10 from applying a torque above the predetermined amount to the fastener 100.

In one embodiment, the entire shaft 30 is constructed of a material that elastically deforms under the application of torque. In one embodiment and using the shaft 30 illustrated in FIG. 1, this includes the entire length extending from the handle 20 to the tip 40. In one embodiment, a limited length of the shaft 30 is constructed of this material. The limited length may be located in proximity to the handle 20, within a central section, or in proximity to the tip 40. In one embodiment, two or more sections elastically deform under application of a predetermined torque. In one embodiment as illustrated in FIG. 9, the width of the shaft 30 may affect the elastic deformation. In this embodiment, the neck 35 has a smaller width then either of sections 31, 32 and thus elastically deforms. In one embodiment, the deformation of the shaft 30 is limited to the neck 35. In another embodiment, a majority of the deformation occurs in the neck 35 with a lesser amount of deformation occurring within the first and second sections 31, 32. In one embodiment, the shaft 30 returns to the original shape after the torque is removed. In one embodiment, the shaft 30 is plastically deformable when subjected to the predetermined amount of torque. Plastically deformed shafts 30 may be discarded after use.

In one embodiment, the combination of the bending shaft 30 and the geometry of the tip 40 prevent application of excessive torque. Prior to applying torque, the shaft 30 includes a shape to engage the tip 40 with the fastener 100. In one embodiment, the shaft 30 is substantially straight. In other embodiments, the shaft 30 may be curved. In this first orientation, the tip 40 engages the fastener 100 and torque applied through to the shaft 30 causes rotation and insertion of the fastener 100 into the support member 300. The shaft 30 has a rotational stiffness to transfer the torque applied to the shaft 30 to the fastener 100. In one embodiment, an additional downward force into the support member 300 also drives the fastener 100 during insertion. As torque increases and the shaft 30 elastically deforms, the geometry of the tip 40 causes it to become mis-aligned with the fastener 100 and thus to disengage.

Figure 10A:
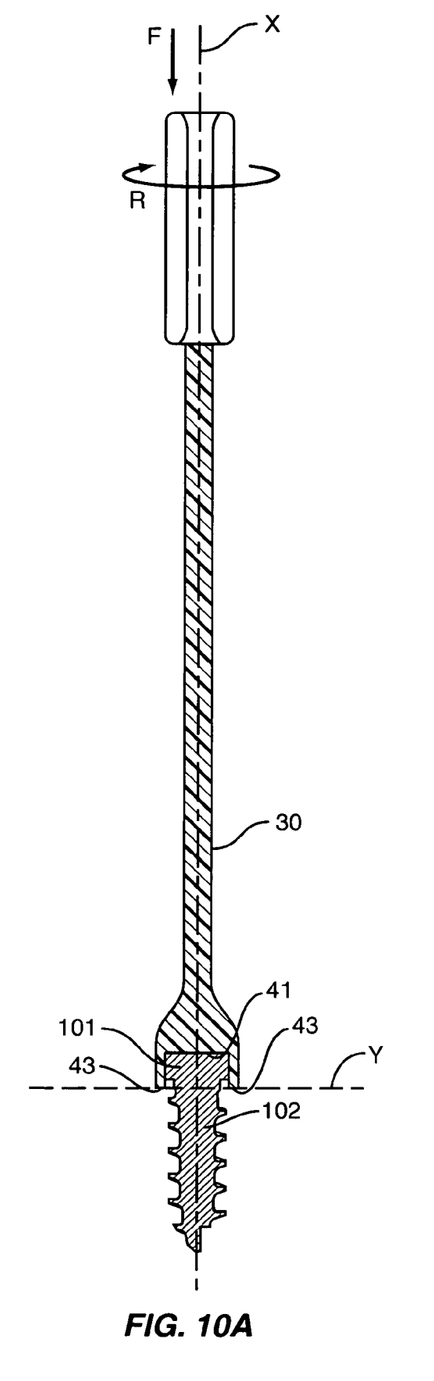
FIGS. 10A and 10B are side schematic views illustrating a method of inserting a fastener according to one embodiment.

FIGS. 10A and 10B illustrate one embodiment of fastener insertion. As illustrated in FIG. 10A, the tip 40 is engaged with the fastener 100 while the shaft 30 is in a first orientation. Specifically, the head 101 of the fastener 100 is inserted within the aperture 41 while the shaft 30 is substantially straight. In one embodiment, a reference line X extends through a center of the shaft 30, and the distal edge 43 is aligned along line Y. In one embodiment, line Y and line X are substantially perpendicular. The surgeon may grip and manipulate the handle 20 to engage the tip 40 with the fastener 100.

After engagement, the handle 20 is rotated causing the fastener 100 to move into the support member 300 (not illustrated). In addition to rotation, a downward force F may be applied to the shaft 30 which additionally inserts the fastener 100. In one embodiment, the force F and the rotation are both provided by the surgeon through the handle 20. In one embodiment, the shaft 30 remains in a substantially straight orientation during the insertion of the fastener 100. This may include increasing amounts of torque as the fastener 100 is further inserted into the member 300.

Figure 10B:
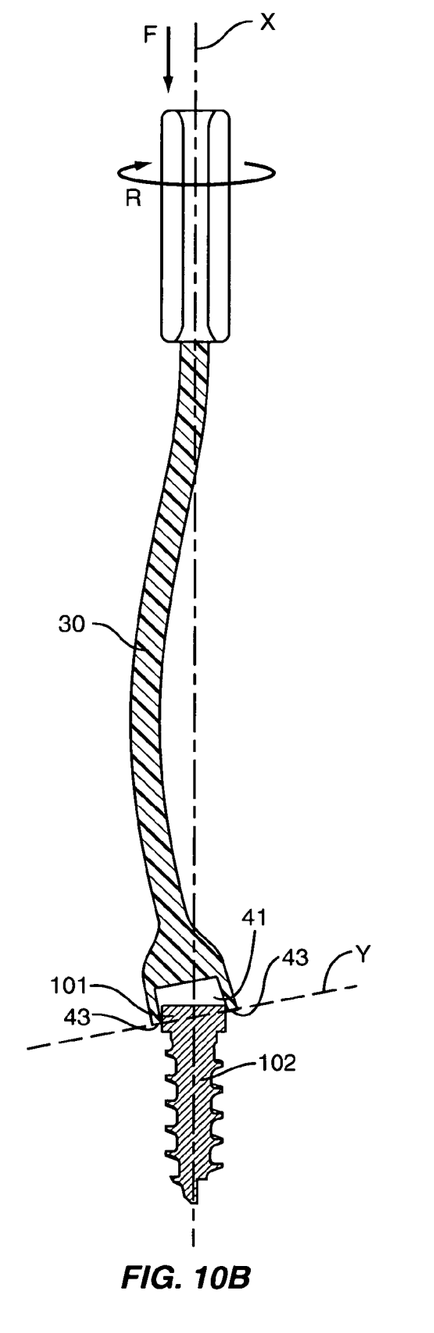

At some point during the insertion, the amount of torque necessary to further insert the fastener 100 may exceed a predetermined amount. This causes the shaft 30 to elastically deform as illustrated in FIG. 10B. In one embodiment, the rotation itself causes the elastic deformation. In one embodiment, the rotation in combination with the downward force F causes the elastic deformation. In one embodiment, the elastic deformation causes the shaft 30 to bend away from the reference line X. This further causes the tip 40 to move and causes the distal edge 43 defined by line Y to move. This movement causes the tip 40 to begin to disengage from the fastener 100. Specifically as illustrated in FIG. 10B, the aperture 41 moves away from the head 101. At some point of elastic deformation, the aperture 41 disengages from the head 101 preventing additional torque from being applied to the fastener 100. In one embodiment, the shaft 30 returns to the original orientation after the torque is removed.

In one embodiment, in addition to the elastic deformation of the shaft 30, the tip 40 experiences plastic deformation to prevent further engagement. In a first orientation prior to the application of torque, the tip 40 is sized and shaped to engage with the head 101. After the predetermined amount of torque is exceeded, the tip 40 plastically deforms to a shape and/or size that causes it to disengage from the head 101. The amount of torque necessary to plastically deform the tip 40 may be substantially equal to the amount necessary to elastically deform the shaft 30, or may be more or may be less. In one embodiment, the amount of torque necessary to deform the shaft 30 is less than the amount necessary to deform the tip 40. In one embodiment, amount of torque necessary to deform the tip 40 is less than the amount necessary to deform the shaft 30. In one embodiment, the shaft 30 and tip 40 deform at substantially the same amount of torque.

The screwdriver 10 may be used in a number of surgical contexts. One context includes driving a fastener 100 to attach a surgical plate within a patient. The fastener 100 extends through an aperture in the plate and attaches the plate to a support member, such as a vertebral member, within the patient.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical device to drive a medical fastener within a patient comprising:
    an elongated shaft including a proximal end and a distal end; and
    a tip at the distal end sized to engage the fastener, the tip including a distal edge;
    the shaft being substantially straight when no torque is applied to the shaft with a reference line extending longitudinally along the shaft when the shaft is substantially straight, the distal edge being substantially perpendicular to the reference line;
    the shaft including a curved shape extending along the entire length thereof when a predetermined amount of torque is applied with the distal edge being positioned at a non-perpendicular angle relative to the reference line;

the tip constructed of a deformable material that deforms from a first shape to a second shape when a specified amount of torque is applied to the shaft.

2. The device of claim 1, further comprising a handle attached to the proximal end of the shaft, the handle comprising a larger width than the shaft.

3. The device of claim 1, wherein the tip comprises a receiver opening including a depth to extend into the shaft from the distal end with the distal edge comprising an exterior of the receiver opening.

4. The device of claim 3, wherein the receiver opening includes a first shape prior to the application of the specified amount of torque and a second different shape after the application of the specified amount of torque.

5. The device of claim 1, wherein the tip extends outward from the distal end of the shaft.

6. The device of claim 1, wherein the shaft and the tip are constructed from a common material.

7. The device of claim 1, wherein the predetermined amount of torque and the specified amount of torque are substantially the same.

8. A surgical device to drive a medical fastener within a patient comprising:
an elongated shaft including a proximal end and a distal end, the shaft being constructed of a deformable material; and
a tip including a distal edge positioned at the distal end of the shaft and being sized to engage the fastener, the tip being constructed of a deformable material;
the shaft and the tip each comprising first shapes when no torque is applied to the shaft and each including different shapes when the predetermined amount of torque is applied to the shaft such that the tip is moved out of engagement with the fastener.

9. The device of claim 8, wherein the shaft is substantially straight when no torque is applied to the shaft and is curved when the predetermine amount of torque is applied to the shaft.

10. The device of claim 8, wherein the tip comprises an aperture that extends into the shaft from the distal end.

11. A surgical device to drive a medical fastener within a patient comprising:
an elongated, longitudinally solid, and hollow shaft including a proximal end and a distal end; and
a tip positioned at the distal end of the shaft and being sized to engage the fastener;
the elongated shaft being substantially straight to allow the tip to engage with the fastener when less than a predetermined amount of torque is applied to the shaft and a deformed shape when more than the predetermined amount of torque is applied to the shaft to prevent the tip from engaging with the fastener;
the tip constructed of a deformable material that deforms from a first shape to a second shape when the shaft is in the deformed shape.

12. The device of claim 11, wherein the shaft is constructed of a non-metallic material.

13. A surgical device to drive a medical fastener within a patient comprising:
an elongated shaft including a proximal end and a distal end, the shaft constructed of a first material; and
a tip positioned at the distal end of the shaft and being sized to engage the fastener, the tip constructed of a second material;
both the first and second materials becoming deformed upon the application of an excessive amount of torque with the shaft and the tip each comprise first shapes upon the application of no torque with the first shapes allowing the tip to engage with the fastener;
each of the tip and the shaft deforming to different shapes upon the application of the excessive amount of torque with the different shapes preventing the tip from being engaged with the fastener.

14. The device of claim 13, wherein the first material deforms upon the application in excess of a first torque amount and the second material deforms upon the application in excess of a second, different torque amount.

15. A method of driving a medical fastener into a support member within a patient, the method comprising the steps of:
engaging a tip of a shaft with the fastener with the tip engaging the fastener at a first angular position;
applying a first torque to the shaft with the tip engaging the fastener at the first angular position and driving the fastener into the support member;
applying a second greater torque to the shaft and deforming the shaft into a bent shape to cause the tip to engage the fastener at a second angular position while continuing to drive the fastener into the support member;
applying a third even greater torque to the shaft and deforming the shaft a greater amount to cause the tip to move beyond the second angular position, to move along a surface of the fastener, and to disengage from the fastener; and
while driving the fastener into the support member, deforming the tip to further disengage the tip from the fastener.

16. The method of claim 15, wherein the shaft is substantially straight when engaging the tip with the fastener at the first angular position.

17. The method of claim 15, further comprising applying an axial force to the shaft while applying the first, second, and third amounts of torque.

18. A method of driving a medical fastener into a support member within a patient, the method comprising the steps of:
engaging a tip at a distal end of a substantially straight shaft with the fastener;
applying a first torque to the shaft and rotating the fastener with the shaft remaining substantially straight;
applying a second greater torque to the shaft and rotating the fastener and bending the shaft a first amount; and
applying a third even greater torque to the shaft and bending the shaft beyond the first amount and deforming the tip and disengaging the tip from the fastener.

19. The method of claim 18, wherein the step of engaging the tip with the fastener comprises inserting the fastener into an aperture in the distal end and contacting an edge of the aperture with the fastener.

20. The method of claim 18, wherein the step of bending the shaft beyond the first amount causes the tip to slide off of the fastener.

21. The method of claim 18, further comprising applying the second greater torque to the shaft and deforming the tip and maintaining the tip engaged with the fastener.

22. A method of driving a medical fastener into a support member within a patient, the method comprising the steps of:
engaging a tip at a distal end of a shaft with the fastener;
applying a torque to the shaft and rotating the fastener into the support member;
increasing the torque applied to the shaft and deforming the shaft and the tip to disengage the tip from the fastener and preventing the torque transferred to the fastener from exceeding a predetermined; and,
wherein both of the shaft and the tip being deformed with one of the shaft and the tip beginning to deform prior to the other.

23. The method of claim 22, further comprising beginning to deform the shaft prior to beginning to deform the tip.

24. The method of claim 22, further comprising beginning to deform the tip prior to beginning to deform the shaft.

25. The method of claim 22, further comprising gradually increasing the torque applied to the shaft and gradually deforming the shaft.

26. The method of claim 22, further comprising gradually increasing the torque applied to the shaft and gradually deforming the tip.

* * * * *